United States Patent [19]

Hallgren

[11] 4,129,574
[45] Dec. 12, 1978

[54] METHOD FOR MAKING CYCLIC CARBONATES AND POLYMERS THEREFROM

[75] Inventor: John E. Hallgren, Scotia, N.Y.

[73] Assignee: General Electric Company, Schenectady, N.Y.

[21] Appl. No.: 804,938

[22] Filed: Jun. 9, 1977

[51] Int. Cl.² ............................................. C07D 323/00
[52] U.S. Cl. ................................................. 260/340.2
[58] Field of Search ...................................... 260/340.2

[56] References Cited

U.S. PATENT DOCUMENTS

| | | | |
|---|---|---|---|
| 3,137,706 | 6/1964 | Prochaska | 260/340.2 |
| 3,155,683 | 11/1964 | Moody | 260/340.2 |
| 3,274,214 | 9/1966 | Prochaska | 260/340.2 |

*Primary Examiner*—Norma S. Milestone
*Attorney, Agent, or Firm*—William A. Teoli; Joseph T. Cohen; Charles T. Watts

[57] ABSTRACT

A method is provided for making cyclic carbonates of 2,2-bis(4-hydroxyphenyl)-1,1-dichloroethylene, such as the cyclic trimer, by effecting the polymerization of the aforementioned bis(4-hydroxyphenyl)dichloroethylene to a linear polycarbonate, and then agitating a solution of the resulting polycarbonate in the presence of a tertiary organic amine. The cyclic carbonates made by the aforementioned process are useful as flame retardants in polycarbonates.

6 Claims, No Drawings

METHOD FOR MAKING CYCLIC CARBONATES AND POLYMERS THEREFROM

The present invention relates to a method for making cyclic carbonates from 2,2-bis(4-hydroxyphenyl)-1,1-dichloroethylene by initially forming a linear polycarbonate and thereafter converting the resulting polymer in the presence of a tertiary organic amine to the cyclic state.

The cyclic carbonates made in accordance with the method of the present invention have the formula,

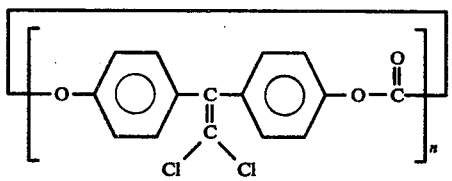

where n is an integer equal to 3 or 4. The cyclic carbonates of formula (1) can be employed as flame retardants when incorporated into thermoplastic organic polymers, such as Lexan polycarbonate, Valox polyester, which are thermoplastics manufactured by the General Electric Company, high impact polystyrene, etc. The cyclic carbonates of formula (1) can be made by phosgenating a mixture of a bisphenol of the formula,

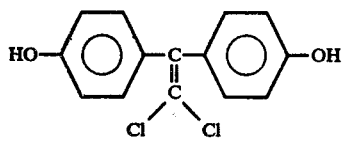

water, organic solvent, sodium hydroxide and a tertiary organic amine. Phosgenation of a bisphenol of formula (2) is shown by Z. Wielgosz and S. Porejko, "Synthesis and Properties of Polycarbonates from Chlorobisphenols", Polimery-Tworzywa Wielkoczasteczkowe, 1971, pages 495–500. I have found that in instances where a bisphenol of formula (2) was phosgenated in an aqueous basic medium containing an organic solvent and a tertiary organic amine to produce cyclic carbonates of formula (1), a relatively low yield of cyclic carbonate, such as 18%, is obtained. Cyclic carbonates of bisphenol-A, also can be made directly from bisphenol-A by phosgenation procedures, such as shown in U.S. Pat. Nos. 3,155,683 and 3,211,025.

The present invention is based on the discovery that cyclic carbonates of formula (1) can be made in yields as high as 95% or greater by initially phosgenating bisphenols of formula (2) in the presence of an aqueous alkali hydroxide and a tertiary amine catalyst to produce linear polycarbonate, effecting the removal of the aqueous phase from the resulting reaction mixture and thereafter agitating the organic phase in the presence of tertiary organic amine catalyst.

In the practice of the invention, there is provided a method for making cyclic carbonates of formula (1) which comprises
(A) phosgenating a mixture of a bisphenol of formula (2), an organic solvent, water and a tertiary organic amine catalyst to produce a polycarbonate,
(B) effecting the removal of the aqueous layer from the mixture of (A),
(C) agitating the organic phase remaining from (B) in the presence of an effective amount of a tertiary organic amine, and
(D) removing cyclic carbonate of formula (1) from the mixture of (C).

Included by the tertiary organic amines which can be employed in the method of the practice of the present invention are, for example, triethylamine, N-methyl piperidine, lutedine, diisopropylethylamine, pyridine, tributylamine, etc. Included by the organic solvents which can be used in the practice of the present invention are, for example, methylene chloride, chloroform, tetrahydrofuran, chlorobenzene, dioxane, dichlorobenzene, trichloroethylene, etc. Some of the alkali metal hydroxides which can be used in the practice of the method of the present invention are, for example, sodium hydroxide, potassium hydroxide, calcium hydroxide, etc.

In the practice of the invention, the cyclic carbonates of formula (1) can be made by initially polymerizing the bisphenol of formula (2) to polycarbonate and thereafter agitating an organic solvent solution of the polycarbonate in the presence of a tertiary organic amine catalyst. During phosgenation, the mixture is agitated and agitation can be continued after the phosgenation has been completed. The mixture is allowed to settle and the organic phase is recovered. The organic phase is then agitated at a temperature in the range of 0° C. to 200° C. while maintaining an effective amount, such as 0.1 to 10%, of tertiary organic amine in the mixture. After the mixture has been agitated sufficiently, cyclic trimer can be separated from the mixture by filtration, where the amount of trimer formed is dependent on time and temperature to effect the separation of the cyclic. In instances where cyclic tetramer recovery is desired, the reaction mixture can be filtered, poured into a $C_{(5-15)}$ hydrocarbon solvent, such as hexane, followed by filtering the hydrocarbon phase and stripping the hydrocarbon solvent containing the cyclic tetramer therefrom. A molecular sieve can be used to facilitate drying.

Phosgenation of the mixture of the bisphenol of formula (1) can be performed at a temperature in the range of from 25° C. to 75° C. There can be employed from 20 to 50% by weight of alkali hydroxide, or 0.5 to 5% of tertiary organic amine, based on the weight of the mixture.

The cyclic carbonates made in accordance with the practice of the present invention can be employed as intermediates for making polycarbonate substantially free of impurities normally associated with such polycarbonate made by direct phosgenation from the bisphenol of formula (2). In addition, the cyclic carbonates can be employed as flame retardants when used with bisphenol-A polycarbonates at from 5 to 30% by weight of cyclic carbonates, based on the total weight of the cylic carbonate-polycarbonate blend.

In order that those skilled in the art will be better able to practice the invention, the following examples are given by way of illustration and not by way of limitation. All parts are by weight.

EXAMPLE 1

A mixture of 1,1-bis(4-hydroxyphenyl)-2,2-dichloroethylene, 0.05 parts triethylamine, 12 parts of methylene chloride and 1 part of sodium hydroxide pellets was phosgenated over a period of 20 minutes while the mixture was stirred at a temperature of 25°-35° C. The phosgene addition was terminated and the mixture was stirred for an additional 5 minutes. The mixture was then acidified, washed twice with water, then poured into 50 parts of methanol to produce 1.1 part of polycarbonate which represented a yield of 92%.

A mixture of 0.5 part of the above polycarbonate, 13 parts of methylene chloride and 0.1 part of triethylamine was stirred for 66 hours under nitrogen and under ambient conditions. A white precipitate formed and the mixture was filtered under vacuo. A precipitate was washed with methylene chloride and ether and dried under reduced pressure at 100° C. to provide 0.48 part of product, representing a yield of 97%. Based on its IR spectrum and further confirmed by NMR, GPC and MS the product was the cyclic trimer of formula (1).

EXAMPLE 2

In accordance with the procedure of Example 1, several tertiary organic amines were employed at different concentrations and methylene chloride solutions of the polycarbonate of Example 1. The following results were obtained, where "Polycarbonate" indicates the parts of polycarbonate employed in the mixture, "& Solids" indicates the total content of the solids in the mixture, "Organic Amine" indicates the percent by weight of the tertiary organic amine employed in the mixture, "Time" indicates the time in hours the mixture was stirred under ambient conditions and "Yield" indicates the percent by weight of cyclic trimer recovered from the mixture.

| Poly-carbonate | % Solids | Organic Amine | Time | Yield |
|---|---|---|---|---|
| 4 | 17 | 2,2,6,6,N-pentamethyl-piperidine (20) | 40 | 38% |
| 0.5 | 5 | $(C_2H_5)_3N$ (20) | 66 | 98% |
| 50 | 5 | $(C_2H_5)_3N$ (20) | 16 | 99% |
| 120 | 8 | $(C_2H_5)_3N$ (20) | 16 | 96% |
| 2 | 5 | $(C_2H_5)_3N$ (20) | 16 | 91% |

The above results show that solids concentration has a significant effect on yield of cyclic trimer.

EXAMPLE 3

Polycarbonate of the bisphenol of formula (2) was prepared in accordance with the procedure of Example 1. The polycarbonate was dissovled in 100 parts by weight of dichlorobenzene, and 0.5 parts 2,2,6,6,N,-pentamethylpiperdine added. The mixture was then refluxed to a temperature of up to 180° C., resulting in the production of dichlorobenzene solution of various polycarbonates. The mixture was allowed to cool to ambient temperatures. It was then poured into hexane, and thereafter filtered. The filtrate was evaporated to dryness to provide a 60% yield of a cyclic. Based on its IR, NMR and MS spectra, the cyclic was the tetramer of formula (1), as shown by the formula,

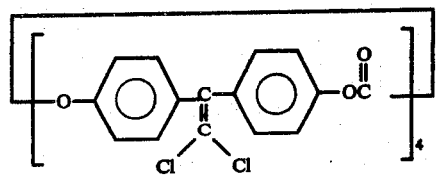

EXAMPLE 4

A mixture consisting of 10 parts of the cyclic trimer of formula (1), 0.174 part of p-cumylphenylcarbonate, 0.78 part of 2,2,6,6,N-pentamethylpiperdine and 130 parts of o-dichlorobenzene was heated to reflux with stirring under nitrogen for 1 hour. Complete solution of the mixture occurred and it was heated for an additional 3 hours with stirring and thereafter allowed to cool to room temperature. The mixture was then extracted three times with about 500 parts of a 1% aqueous HCl solution, followed by three times with distilled water. The solution was filtered, then precipitated by pouring it into excess methanol. There was obtained a stringy product which was dried at 100° C. for 2 hours, then dissolved in methlene chloride, then filtered and reprecipitated. After being dried for 24 hours at 60° C., there was obtained 9.3 parts or a 93% yield of a white stringy product. Based on method of preparation, the product was a polycarbonate and it had an intrinsic viscosity of 0.43, $\overline{M}_n = 18,270$, $\overline{M}_w = 73,100$, $\overline{M}_w/\overline{M}_n = 4$. The above procedure was repeated, except that 0.01 part of cyclic tetramer was employed in ortho-dichlorobenzene and the mixture heated to 100° C. After 2 hours, the gel permiation chromatograph (GPC) showed the presence of a high molecular weight polymer having $\overline{M}_n$ of about 25,000 and the disappearance of the cyclic tetramer. The high molecular weight polymer consisted essentially of chemically combined units of the formula,

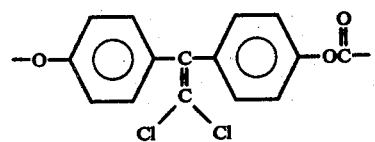

EXAMPLE 5

A mixture of 2.0 part of polycarbonate of Example 1, 40 parts of methylene chloride and 0.5 part of triethylamine was allowed to stir for 18 hours under ambient conditions. A copious white precipitate formed and the mixture was filtered under reduced pressure. The precipitate was washed with methylene chloride, followed by ether and dried in vacuo at 70° C. There was obtained 1.82 parts or 91% yield of the cyclic trimer included by formula (1). The identity of the trimer was confirmed by its IR, NRM, GPC and MS spectra.

In addition to example 4, polycarbonates consisting essentially of chemically combined units of the formula,

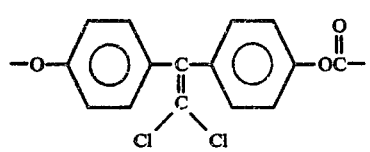

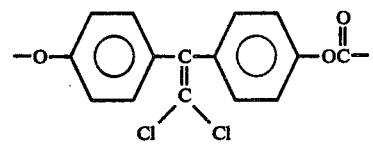

can be made by agitating a mixture of cyclic carbonate of formula (1) and an organic solvent in the presence of an effective amount of a tertiary organic amine and from about 1 to 10 mol percent based on total moles of carbonate units in the mixture of a $C_{(6-20)}$ aryl carbonate, at a temperature in the range of from 0° C. to 300° C.

As shown in copending applications RD-9080 of Keith N. Sannes, and my copending application RD-9987, both applications being filed concurrently herewith and assigned to the same assignee as the present invention, cyclic trimers and higher cyclics are described respectively as well as methods for making such materials.

Although the above examples are directed to only a few of the very many variables which can be employed in the practice of the method of the present invention, it should be understood that a mcuh broader variety of organic solvents and tertiary organic amines can be utilized to produce cyclopolycarbonates, as shown by formula (1).

What I claim as new and desire to secure by Letters Patent of the United States is:

1. A method for making cyclic carbonates of the formula,

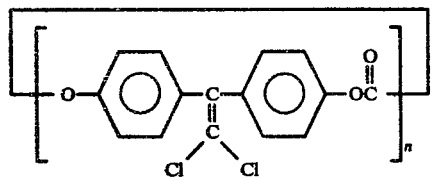

where n is 3 or 4, which comprises (1) agitating at a temperature in the range of from 0° C. to 200° C., an organic solvent solution of a linear polycarbonate consisting essentially of chemically combined units of the formula, in the presence of an effective amount of a tertiary organic amine catalyst, and (2) removing the precipitated cyclic carbonate trimer from the mixture of (1).

2. A method for making cyclic carbonates of the formula,

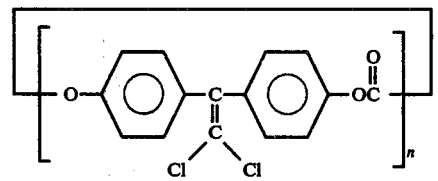

where n is an integer equal to 3 or 4, which comprises (A) phosgenating a mixture of a phenol of the formula,

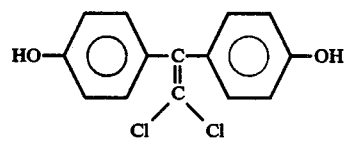

an organic solvent, water and tertiary organic amine catalyst to produce a polycarbonate, (B) effecting the removal of the aqueous layer from the mixture of (A), (C) agitating the organic phase remaining from (B) at a temperature in the range of from 0° to 200° C. in the presence of an effective amount of a tertiary organic amine and (D) removing the precipitated cyclic carbonate trimer from the mixture of (C).

3. A method in accordance with claim 1, where the tertiary organic amine is triethylamine.

4. A method in accordance with claim 1, where the organic solvent is methylene chloride.

5. A method in accordance with claim 1, where a $C_{(5-15)}$ hydrocarbon solvent is utilized in the reaction mixture following the removal of the precipitated cyclic carbonate and the resulting hydrocarbon phase is filtered and stripped of hydrocarbon solvent to effect the recovery of cyclic carbonate tetramer.

6. A method in accordance with claim 2, where a $C_{(5-15)}$ hydrocarbon solvent is utilized in the reaction mixture following the removal of the precipitated cyclic carbonate and the resulting hydrocarbon phase is filtered and stripped of hydrocarbon solvent to effect the recovery of cyclic carbonate tetramer.

* * * * *